: US 10,351,508 B2
(45) Date of Patent: Jul. 16, 2019

(12) United States Patent
Il et al.

(54) CARBONATE ESTER PURIFICATION METHOD, CARBONATE ESTER SOLUTION PRODUCTION METHOD, AND CARBONATE ESTER PURIFICATION APPARATUS (71) Applicant: UBE INDUSTRIES, LTD., Ube-shi, Yamaguchi (JP)

(72) Inventors: Hirofumi Il, Ube (JP); Yuya Fukui, Ube (JP); Yohei Shimasaki, Ube (JP); Koji Okano, Ube (JP); Koji Takebayashi, Ube (JP); Naoto Nakao, Ube (JP)

(73) Assignee: UBE INDUSTRIES, LTD., Yamaguchi (JP)

( * ) Notice: Subject to any disclaimer, the term of this patent is extended or adjusted under 35 U.S.C. 154(b) by 3 days.

(21) Appl. No.: 15/538,634

(22) PCT Filed: Dec. 25, 2015

(86) PCT No.: PCT/JP2015/086359
§ 371 (c)(1),
(2) Date: Jun. 21, 2017

(87) PCT Pub. No.: WO2016/104760
PCT Pub. Date: Jun. 30, 2016

(65) Prior Publication Data
US 2017/0355659 A1    Dec. 14, 2017

(30) Foreign Application Priority Data

Dec. 26, 2014  (JP) .................................. 2014-265493

(51) Int. Cl.
*C07C 68/08* (2006.01)
*C07C 69/96* (2006.01)

(52) U.S. Cl.
CPC .............. *C07C 68/08* (2013.01); *C07C 69/96* (2013.01)

(58) Field of Classification Search
CPC ......... C07C 68/08; C07C 69/96; B01D 3/009; B01D 3/143; B01D 3/16; B01D 3/343; B01D 3/42
See application file for complete search history.

(56) References Cited

U.S. PATENT DOCUMENTS

2007/0082985 A1* 4/2007 Buchold ................ C07C 68/00
                                                              524/117

FOREIGN PATENT DOCUMENTS

JP    H03-120240 A    5/1991
JP    H05-201932 A    8/1993
(Continued)

OTHER PUBLICATIONS

Jun. 27, 2017 International Preliminary Report on Patentability issued in International Patent Application No. PCT/JP2015/086359.
(Continued)

*Primary Examiner* — Renee Robinson
*Assistant Examiner* — Derek N Mueller
(74) *Attorney, Agent, or Firm* — Oliff PLC (57) ABSTRACT

Provided is a carbonate ester purification apparatus including a treatment part for mixing a first solution containing a carbonate ester and an acidic substance with an alcohol solution of a metal alcoholate to obtain a mixed solution containing a reaction product of the acidic substance and the metal alcoholate, a separation part for removing a metal salt contained in the reaction product from the mixed solution to obtain a second solution, and a distillation part for removing a component from the second solution, the component different in boiling point from the carbonate ester to obtain (Continued)

a carbonate ester solution, wherein a content of the metal alcoholate in the alcohol solution is 5 to 18 mass %.

4 Claims, 2 Drawing Sheets

(56) References Cited

FOREIGN PATENT DOCUMENTS

| | | |
|---|---|---|
| JP | H06-092905 A | 4/1994 |
| JP | 2004-323371 A | 11/2004 |
| JP | 2004-323470 A | 11/2004 |
| JP | 2014-162746 A | 9/2014 |

OTHER PUBLICATIONS

Mar. 22, 2016 International Search Report issued in International Patent Application No. PCT/JP2015/086359.

\* cited by examiner

CARBONATE ESTER PURIFICATION METHOD, CARBONATE ESTER SOLUTION PRODUCTION METHOD, AND CARBONATE ESTER PURIFICATION APPARATUS

TECHNICAL FIELD

The present disclosure relates to a carbonate ester purification method, a carbonate ester solution production method and a carbonate ester purification apparatus.

BACKGROUND ART

A carbonate ester is a compound useful as a synthetic raw material for aromatic polycarbonates and pharmaceuticals and agricultural chemicals. A known process for producing a carbonate ester is one that carries out synthesis by a gas phase reaction using carbon monoxide and nitrite in the presence of a platinum group metal solid catalyst (see, for example, Patent Literatures 1 and 2). In such a process, a carbonate ester can be obtained by the following reaction formula (i):

$$CO + 2RONO \rightarrow ROC(=O)OR + 2NO \quad (i)$$

In the production methods of Patent Literatures 1 and 2, an intended compound is produced by a catalytic reaction while recycling alkyl nitrite as a raw material. In such a production method, a target compound can be mass produced by scaling up an apparatus.

Patent Literature 2 proposes a technology for preventing the catalytic activity reduction by detecting a concentration of nitrogen monoxide in a supplied gas and adjusting an amount of the molecular oxygen to be supplied based on the obtained concentration. Patent Literature 3 proposes a technology for removing a by-produced halide (see, e.g., Patent Literature 3).

CITATION LIST

Patent Literature

Patent Literature 1: Japanese Unexamined Patent Publication No. 2004-323470
Patent Literature 2: Japanese Unexamined Patent Publication No. 2014-162746
Patent Literature 3: Japanese Unexamined Patent Publication No. H6-92905

SUMMARY OF INVENTION

Technical Problem

In the conventional carbonate ester production method, the water and alcohol are distilled out in a distillation column to remove water and alcohol accompanying a carbonate ester so that impurities contained in the carbonate ester solution are reduced. However, the carbonate ester solution obtained by such a process contains a small amount of impurities derived from a side reaction and hard to reduce in the distillation column.

Carbonate esters, however, have been studied to be used in various fields such as the electrolyte of a lithium ion battery in addition to the synthetic raw material such as pharmaceuticals and agricultural chemicals. Accordingly, there is a demand for establishment of a technology for producing a carbonate ester solution with sufficiently reduced impurities.

An object of one aspect of the present invention is to provide a carbonate ester purification method and a carbonate ester purification apparatus capable of reducing impurities. An object of another aspect of the present invention is to provide a production method capable of producing a carbonate ester solution with reduced impurities.

Solution to Problems

One aspect of the present invention provides a carbonate ester purification method comprising an alkali treatment step of mixing a first solution containing a carbonate ester and an acidic substance with an alcohol solution of a metal alcoholate to obtain a mixed solution containing a reaction product of the acidic substance and the metal alcoholate, a removal step of removing a metal salt contained in the reaction product from the mixed solution to obtain a second solution containing the carbonate ester, and a distillation step of fractionating the second solution to remove a component from the second solution, the component having different boiling point from the carbonate ester, wherein a content of the metal alcoholate in the alcohol solution is 5 to 18 mass %.

In the above purification method, the alkali treatment step is carried out using the alcohol solution containing a metal alcoholate. In the alkali treatment step, a metal salt is produced as the reaction product of the acidic substance and the metal alcoholate. In the removal step, the second solution with a lower content of the acidic substance than in the first solution can be obtained by removing the metal salt. Further, in the distillation step, the impurities different from the carbonate ester can be reduced from the second solution. Additionally, the production of by-products, which are to be impurities in the second solution, can be prevented while allowing the reaction of the acidic substance and the metal alcoholate to proceed sufficiently, because a content of the metal alcoholate in the alcohol solution is within the predetermined range. Consequently, the impurities in the carbonate ester can be reduced.

Another aspect of the present invention provides a carbonate ester solution production method comprising an alkali treatment step of mixing a first solution containing a carbonate ester and acidic substance with an alcohol solution of a metal alcoholate to obtain a mixed solution containing a reaction product of the acidic substance and the metal alcoholate, a removal step of removing a metal salt contained in the reaction product from the mixed solution to obtain a second solution containing the carbonate ester, and a distillation step of fractionating the second solution to remove a component from the second solution, the component having different boiling point from the carbonate ester to obtain a carbonate ester solution, wherein a content of the metal alcoholate in the alcohol solution is 5 to 18 mass %.

In the above production method, the alkali treatment step is carried out using the alcohol solution containing a metal alcoholate. In the alkali treatment step, the acidic substance and the metal alcoholate are reacted to form a metal salt. In the removal step, the second solution with a lower content of the acidic substance than in the first solution can be obtained by removing the metal salt. In the distillation step, the impurities different from the carbonate ester can be reduced from the second solution. Additionally, the production of by-products, which are to be impurities, can be prevented while allowing the reaction of the acidic substance and the metal alcoholate to proceed sufficiently, because a content of the metal alcoholate in the alcohol solution is within the predetermined range. Consequently, a carbonate ester solution with reduced impurities can be produced.

The above carbonate ester solution production method, in some embodiments, may have a content of the methoxymethyl methyl carbonate in the carbonate ester solution of less than 2 mass ppm. Thus, when a content of the methoxymethyl methyl carbonate is sufficiently reduced, the carbonate ester solution can be used for various purposes.

Another aspect of the present invention provides a carbonate ester purification apparatus comprising a treatment part for mixing a first solution containing a carbonate ester and an acidic substance with an alcohol solution of a metal alcoholate to obtain a mixed solution containing a reaction product of the acidic substance and the metal alcoholate, a separation part for removing a metal salt contained in the reaction product from the mixed solution to obtain a second solution, and a distillation part for fractionating the second solution to remove a component from the second solution, the component having different boiling point from the carbonate ester, wherein a content of the metal alcoholate in the alcohol solution is 5 to 18 mass %.

The above purification apparatus is provided with the treatment part for mixing the first solution with the alcohol solution containing a metal alcoholate. In the treatment part, the acidic substance and the metal alcoholate are reacted to produce a metal salt. In the separation part, the second solution with a lower content of the acidic substance than in the first solution can be obtained by removing the metal salt. In the distillation part, the impurities different from the carbonate ester can further be reduced from the second solution by fractionating the second solution. Additionally, the production of by-products, which are to be impurities in the second solution, can be prevented while allowing the reaction of the acidic substance and the metal alcoholate in the treatment part to proceed sufficiently, because a content of the metal alcoholate in the alcohol solution is within the predetermined range. Consequently, the impurities in the carbonate ester can be reduced.

The carbonate ester purification apparatus, in some embodiments, may have a content of the methoxymethyl methyl carbonate in the carbonate ester solution of less than 2 mass ppm. Thus, when a content of the methoxymethyl methyl carbonate is sufficiently reduced, the carbonate ester can be used for various purposes.

Advantageous Effects of Invention

According to the present invention, in an aspect, a carbonate ester purification method capable of reducing impurities and a carbonate ester purification apparatus can be provided. The present invention further provides, in another aspect, a production method capable of producing a carbonate ester solution with reduced impurities.

DESCRIPTION OF EMBODIMENTS

An embodiment of the present invention is described in detail in reference to drawings when needed. Note that the following embodiments are examples to illustrate the present invention and not intended to limit the present invention to the following contents. In the description, the elements having the same element and the same function are denoted by the same symbols, and the description thereof that would be redundant is omitted in some cases.

Figure 1:
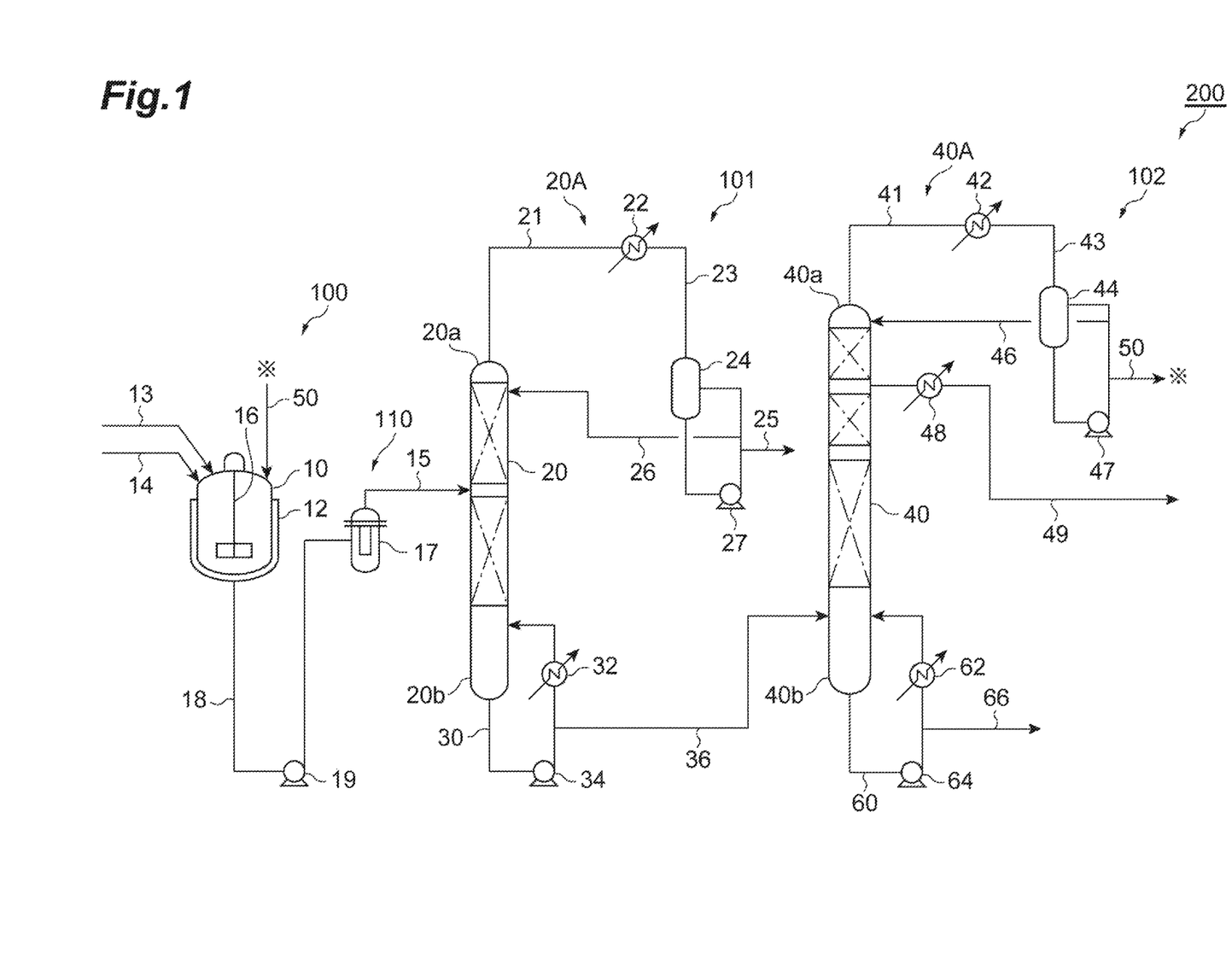
FIG. 1 is a drawing schematically illustrating an embodiment of the carbonate ester purification apparatus.

FIG. 1 is a drawing schematically illustrating an embodiment of the purification apparatus for purifying a carbonate ester. An embodiment of the carbonate ester purification method and the carbonate ester solution production method can use a carbonate ester purification apparatus 200 (carbonate ester solution production apparatus 200) illustrated in FIG. 1.

The carbonate ester purification method of the present embodiment comprises an alkali treatment step of mixing a first solution containing a carbonate ester and an acidic substance and an alcohol solution of a metal alcoholate to obtain a mixed solution containing a reaction product of the acidic substance and the metal alcoholate, a removal step of removing a metal salt contained in the reaction product from the mixed solution to obtain a second solution containing the carbonate ester, and a distillation step of fractionating the second solution to remove a component from the second solution, the component having different in boiling point from the carbonate ester. The distillation step comprises a first distillation step and a second distillation step.

The carbonate ester purification apparatus 200 is provided with a treatment part 100 for carrying out the alkali treatment step, a separation part 110 for carrying out the removal step, and a first distillation part 101 and a second distillation part 102 for carrying out the distillation step. The first solution can be obtained by condensing the product obtained by the gas phase reaction of carbon monoxide and nitrite in the presence of a platinum group metal solid catalyst. The first solution contains, in addition to the carbonate ester as the main component, organic compounds such as alcohols and ethers as the sub-components and acidic substances such as chlorine compounds and nitric acid compounds. Of the sub-components in the first solution, the concentration of the sub-component whose boiling point is greatly different from that of the carbonate ester is adjustable using the distillation columns.

The carbonate ester is, for example, dialkyl carbonates. The two alkyl groups in a dialkyl carbonate molecule may be same or different. Examples of the dialkyl carbonate include dimethyl carbonate, diethyl carbonate, dipropyl carbonate, diisopropyl carbonate, dibutyl carbonate, dipentyl carbonate, dihexyl carbonate, diheptyl carbonate, dioctyl carbonate, dinonyl carbonate, ethyl methyl carbonate, and ethyl propyl carbonate.

Of the dialkyl carbonates, from the viewpoint of the reaction speed of the transesterification and easy removal of a by-produced alkyl alcohol, dialkyl carbonates having a straight chained or branch chained alkyl group having 1 to 10 carbon atoms are preferable, and dimethyl carbonate and diethyl carbonate are more preferable.

The content of the carbonate ester in the first solution is, for example, 98.0 to 99.998 mass %. The first solution contains acidic substances or esters of acidic substances in addition to the carbonate ester. Examples of the acidic substance include hydrochloric acid, nitric acid, nitrous acid, formic acid and mixtures thereof. Examples of the ester of acidic substances include nitric ester and chloroformic ester.

The total content of the chlorine compound and the nitric acid compound (including a nitrous acid compound) in the first solution is, for example, 5 to 100 mass ppm in terms of Cl and $NO_3$ or $NO_2$, respectively. The first solution may contain about 1 to 100 mass ppm of alcohols. Examples of the alcohol include methanol and ethanol.

For the metal alcoholate, it is preferable to use the alcoholate of an alkali metal from the viewpoint of enhancing the reactivity to acidic substances and esters of acidic substances. Examples of the alcoholate of alkali metals include sodium methoxide, sodium ethoxide, potassium methoxide and potassium methoxide. One of these may be used singly or two or more may be used in combination.

The alcohol solution of a metal alcoholate is a solution wherein the above metal alcoholate is dissolved in an alcohol. Various alcohols can be used and, for example, monoalcohols such as methanol, ethanol, propanol or butanol can be used. One of these may be used singly or two or more may be used in combination.

The content of the metal alcoholate in the alcohol solution is 5 to 18 mass %, preferably 5 to 10 mass %. When a content of the metal alcoholate is too high, the side reaction during the alkali treatment step easily proceeds. Accordingly, the impurities different from the carbonate ester tend to be produced easily. On the other hand, when a content of the metal alcoholate is too low, an amount of the alcohol solution for neutralizing the acidic substances becomes too large, and the load to the distillation column for separating the carbonate ester from the alcohol tends to increase.

The treatment part 100 is provided with a treatment tank 10 where the first solution and the alcohol solution of the metal alcoholate are mixed. Pipes 13, 14 are connected to the treatment tank 10. The treatment tank 10 is provided with a jacket 12 for allowing a heat medium to flow therethrough. The first solution is supplied to the treatment tank 10 flowing through the pipe 13. The alcohol solution of the metal alcoholate is supplied to the treatment tank 10 flowing through the pipe 14. In the treatment tank 10, the first solution and the alcohol solution of the metal alcoholate are mixed by a stirrer 16. In the treatment tank 10, the mixed solution is heated to the temperature of the alcohol's boiling point or lower. The acidic substances such as the chlorine compound and the nitric acid compound contained in the first solution and the alcohol solution of the metal alcoholate undergo the neutralization reaction. The acidic substances can be thus reduced in the alkali treatment step.

From the viewpoint of sufficiently reducing the acidic substances, the amount of the alcohol solution of the metal alcoholate to be mixed with the first solution is preferable to be the amount needed to neutralize the acidic substances contained in the first solution or more (neutralization equivalent). The alcohol contained in the alcohol solution can be removed in the distillation column provided on the downstream side.

In the alkali treatment step, a reaction product is produced in the treatment tank 10 due to the neutralization reaction of the acidic substances and the metal alcoholate. Examples of the reaction product include metal salts of inorganic chlorides and inorganic nitric acid compounds. The metal salt deposits in the form of a solid component when the mixed solution in the treatment tank 10 is cooled to, for example, about 30° C. In the removal step, a second solution containing the carbonate ester is obtained by removing the solid component from the mixed solution containing the solid component and the carbonate ester.

In the removal step, the mixed solution is introduced to the separation part 110 flowing through a pipe 18 and a pump 19 connected to the bottom part of the treatment tank 10. A cooler may be provided between the treatment part 100 and the separation part 110. The separation part 110 has a filtering device 17 provided with a filter. The separation part 110 is not particularly limited as long as it has the configuration capable of removing the solid component contained in the mixed solution. In the separation part 110, the second solution containing the carbonate ester as the main component is obtained by removing the solid component. The second solution may contain impurities such as alcohols and water. The impurities may include, in some cases, the trace components contained in the first solution. The content of the carbonate ester in the second solution is, for example, 90 to 99.998 mass %. More specifically, the second solution may contain about 0.002 to 10 mass % of the impurities. Examples of the impurity include nitric acid compounds and organic compounds.

In the first distillation step and the second distillation step, the impurities contained in the second solution are removed by fractionation. Thus, the impurities different in boiling point from the carbonate ester can be removed. The first distillation step and the second distillation step can be carried out using a common distillation column. In the present embodiment, two distillation columns are used to carry out the first distillation step and the second distillation step but the distillation column is not limited to two. Only one column may be used to carry out a single distillation step. Three or more columns may be used to carry out three or more distillation steps.

The second solution obtained in the removal step is introduced to a first distillation column 20 of the first distillation part 101 flowing through a pipe 15. In the first distillation column 20, the impurities such as the alcohol and the carbonate ester are fractionated based on the boiling point differences. The distillate containing the alcohol whose boiling point is lower than the boiling point of the carbonate ester is introduced from a column top part 20a of the first distillation column 20 to a reflux part 20A provided in the first distillation column 20. The reflux part 20A is provided with a condenser 22 for cooling the distillate, a tank 24, a pump 27 and a pipe that connects these mechanical pieces.

The distillate discharged from the column top part 20a of the first distillation column 20 by a pipe 21 is cooled in the condenser 22 to be a condensate and subsequently stored in the tank 24. The condensate containing the alcohol and the like in the tank 24 is returned from the tank 24 to the upper part of the first distillation column 20 via the pump 27 and a pipe 26. Thus, the use of the condensate as the reflux enables an efficient fractionation in the first distillation column 20.

A part of the condensate in the tank 24 is discharged continuously or intermittently via the pump 27 and a pipe 25 to outside of the first distillation column 20. The discharged liquid from the pipe 25 contains, for example, the carbonate ester as the main component and may contain the alcohol, the ether and water as the sub-components. The composition of the discharged liquid is identical with the composition of the reflux liquid that circulates around the reflux part 20A. The content of the organic compounds different from the dimethyl carbonate in the discharged liquid is, for example, 0.01 to 10 mass %. The content of the carbonate ester in the discharged liquid is, for example, 90 to 99.3 mass %. The discharged liquid from the column top part 20a discharged via the pipe 25 may be merged to the alcohol that flows through a pipe 316 or a pipe 319 of a production apparatus 300 of FIG. 2 described later.

Due to the fractionation in the first distillation column 20, the third solution containing the carbonate ester is discharged from a pipe 30 connected to a column bottom part 20b of the first distillation column 20. In the third solution, the components having low boiling points are more reduced than in the first solution. For this reason, the purity of the carbonate ester in the third solution is higher than the first solution.

The purity of the carbonate ester in the third solution is, for example, 99.99 mass % or more. More specifically, in the third solution when compared with the first solution, the content of the trace components such as acidic substances, alcohols and ethers is sufficiently reduced. The carbonate ester solution like this is particularly useful for the purpose where the trace components need to be sufficiently reduced (e.g., the electrolyte of a lithium ion battery).

The third solution discharged from a column bottom part 20b of the first distillation column 20 may contain trace components such as water and alcohols. These trace components can be reduced in the second distillation step. The third solution is supplied to a second distillation column 40 of the second distillation part 102 via a pipe 30, a pump 34 and a pipe 36. A part of the third solution, after heated by the heat exchange with a heat medium at a heat exchanger 32, may be returned to the lower part of the first distillation column 20 as a heat source of the first distillation column 20.

In the second distillation step, the carbonate ester and the trace components contained in the third solution are fractionated based on the boiling point differences in the second distillation column 40. The fluid containing the trace components having higher boiling points than the carbonate ester flows through a pipe 60 connected to a column bottom part 40b of the second distillation column 40 and are discharged via a pump 64 and a pipe 66. A part of the fluid, after heated by the heat exchange with a heat medium at a heat exchanger 62, may be returned to the lower part of the second distillation column 40 as a heat source of the second distillation column 40. An example of the trace component whose boiling point is higher than the carbonate ester is water.

When the third solution contains the trace components whose boiling points are lower than the carbonate ester such as the alcohol (e.g., the alcohol), these trace components are introduced to the reflux part 40A that includes a condenser 42 connected to a column top part 40a of the second distillation column 40 and a tank 44. Specifically, the fluid from the column top part of the second distillation column 40 is cooled in the condenser 42 to be a condensate and subsequently stored in the tank 44. The condensate containing the trace components such as the alcohol in the tank 44 is refluxed from the tank 44 to the second distillation column 40 via a pump 47 and a pipe 46. A part of the condensate in the tank 44 may be allowed to flow through a pipe 50 and be returned to the treatment tank 10 or used for other purposes.

The carbonate ester contained in the third solution is extracted by a side cut from a pipe 49 connected to between the center section and the column top part of the second distillation column 40. The carbonate ester solution extracted by a side cut is cooled in a heat exchanger 48 connected to the pipe 49. Thus, the content of the impurities different from the carbonate ester can be reduced sufficiently. The purity of the carbonate ester in the carbonate ester solution obtained in the second distillation column 40 is, for example, 99.995 mass % or more.

The third solution is fractionated using the second distillation column 40 of the second distillation part 102, thereby obtaining a carbonate ester solution with a lower content of the impurities than in the third solution. The carbonate ester purification apparatus 200 has the treatment tank 10, the filtering device 17, the first distillation column 20 and the second distillation column 40 arranged in series, thereby efficiently producing the high purity carbonate ester solution continuously. Additionally, in the treatment tank 10, the alcohol solution with a content of the metal alcoholate within the predetermined range is used to alkali treat the acidic substances contained in the first solution. Thus, the production of the by-products such as methoxymethyl methyl carbonate can be prevented in the alkali treatment step. As described above, the production of the by-products having about the same boiling points as the carbonate ester is prevented whereby the carbonate ester solution with a sufficiently reduced content of the impurities can be produced. The content of the methoxymethyl methyl carbonate in the carbonate ester solution may be, for example, less than 2 mass ppm or less than 1 mass ppm. The carbonate ester solution with sufficiently reduced impurities like this is particularly useful for the purpose where the trace components need to be sufficiently reduced (e.g., the electrolyte of a lithium ion battery).

It is not indispensable to use two distillation columns as described in the present embodiment and the carbonate ester solution with a sufficiently reduced content of the impurities can be produced using either one of the first distillation part 101 or the second distillation part 102.

Figure 2:
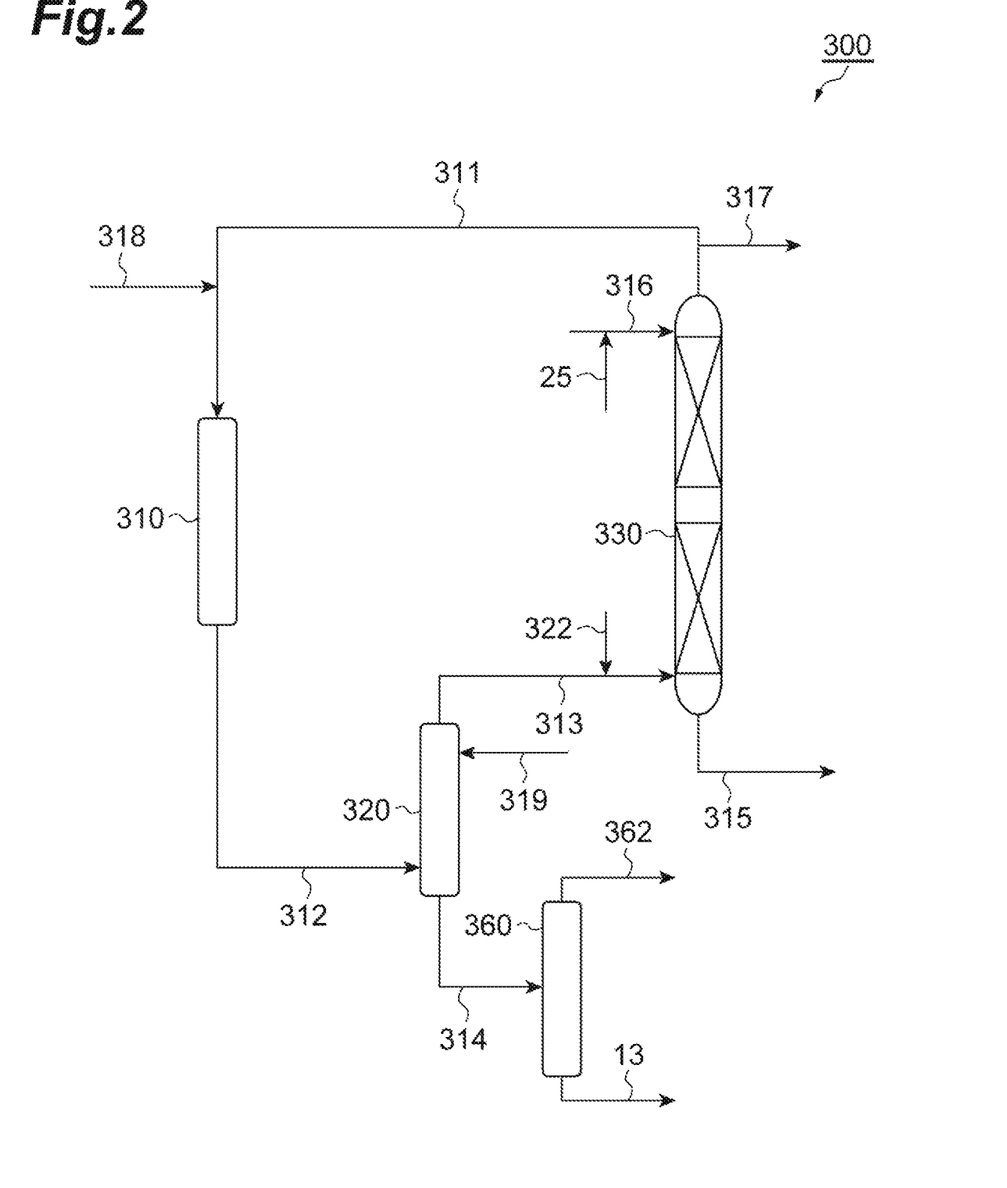
FIG. 2 is an example of an apparatus for producing the first solution containing a carbonate ester and formaldehyde.

FIG. 2 is an example of an apparatus for producing the first solution containing a carbonate ester and formaldehyde. The first solution production apparatus 300 is provided with a first reactor 310 having a catalyst for producing dialkyl carbonate and nitric monoxide by reacting carbon monoxide and alkyl nitrite, in which a second gas containing the dialkyl carbonate and the nitric monoxide is produced from a first gas containing the carbon monoxide, the alkyl nitrite and the nitric monoxide; an absorption column 320, in which the second gas is contacted with an absorbing liquid which absorbs the dialkyl carbonate to separate a condensate containing the dialkyl carbonate from a noncondensable gas containing the nitric monoxide; and a second reactor 330, in which an alcohol and a mixed gas of the noncondensable gas and a molecular oxygen are introduced to react to the nitric monoxide, the molecular oxygen and the alcohol thereby producing a third gas containing the alkyl nitrite and the nitric monoxide.

The first reactor 310 has a carbonate ester production catalyst for producing a carbonate ester and nitric monoxide by reacting carbon monoxide and alkyl nitrite. Examples of the carbonate ester production catalyst include solid catalysts wherein a platinum group metal and/or a compound thereof is supported on a support. The amount of the platinum group metal and/or a compound thereof to be supported in the solid catalyst relative to the support is 0.1 to 10 wt %, preferably 0.5 to 2 wt %. Examples of the support include inert supports such as activated carbons, aluminas (γ-alumina, etc.), zeolites, molecular sieves, spinels (lithium aluminate spinel, etc.). The platinum group metal and a compound thereof are supported on the support by using a known method such as an impregnation method or an evaporation to dryness method.

Examples of the platinum group metal and a compound thereof include platinum metals, palladium metals, rhodium metals and iridium metals. Examples of the platinum group metal compound include inorganic acid salts (nitrates, sulfates, phosphates, etc.), halides (chlorides, bromides, etc.), organic acid salts (acetates, oxalates, benzoates, etc.) and complexes (lithium tetrachloropalladate, sodium tetrachloropalladate) of these metals. Of these, palladium chloride or chlorine-containing complexes of palladium are preferable. The amount of the platinum group metal and/or a compound thereof supported on the support is preferably 0.01 to 10 mass %, more preferably 0.2 to 2 mass %.

The carbonate ester production catalyst may contain, in addition to the platinum group metal and a compound thereof, copper, iron, bismuth or compounds thereof. Of these, chlorides (cuprous chlorides, cupric chlorides, ferrous chlorides, ferric chlorides, bismuth chlorides) are preferable. These amount supported on the support is preferably 1:0.1 to 1:50 as "platinum group metal and a compound thereof": "copper, iron, bismuth and compounds thereof" (in terms of molar ratio of metal atoms), more preferably 1:1 to 1:10.

The preparation method of the catalyst is not limited and, for example, the catalyst can be prepared by allowing a platinum group metal compound to be supported on the support by a known method such as an impregnation method or an evaporation to dryness method and subsequently drying the obtained support.

The first gas containing the carbon monoxide and the alkyl nitrite is introduced into the first reactor 310 provided with the catalyst described above. Accordingly, the gas phase reaction represented by the following formula (I) proceeds. In the formula (I) R represents an alkyl group. The number of carbon atoms of the alkyl group is preferably 1 to 3.

$$CO+2RONO \rightarrow ROC(=O)OR+2NO \qquad (I)$$

The content of the nitric monoxide in the first gas is, for example, 5 to 50 vol % on the basis of the total of the carbon monoxide, the alkyl nitrite and the nitric monoxide. Thus, the first gas contains the nitric monoxide in a higher concentration than the molecular oxygen. For this reason, the nitric monoxide concentration in the first gas can be easily detected with a high accuracy. The content of the carbon monoxide in the first gas is, for example, 30 to 70 vol % on the basis of the total of the carbon monoxide, the alkyl nitrite and the nitric monoxide. The content of the alkyl nitrite in the first gas is, for example, 10 to 50 vol % on the basis of the total of the carbon monoxide, the alkyl nitrite and the nitric monoxide. The first gas may contain an inert gas together with the carbon monoxide, the alkyl nitrite and the nitric monoxide. The concentration of the nitric monoxide in the first gas is preferably 1 to 20 vol % on the basis of the whole first gas. Further, the concentration of the carbon monoxide in the first gas is, for example, 10 to 40 vol % on the basis of the whole first gas.

Due to the reaction represented by the above formula (1), the second gas containing the carbonate ester and the nitric monoxide is produced in the first reactor 310. The concentration of the carbon ester in the second gas is, for example, 1 to 50 vol %, and the concentration of the nitric monoxide is, for example, 1 to 20 vol %, on the basis of the whole second gas. The vol % used herein indicates the volume ratio under the standard conditions (25° C., 100 kPa).

The second gas produced in the first reactor 310 is introduced into the absorption column 320 through a pipe 312. The absorption column 320 may be any gas-liquid contactable column and examples include absorption columns of tray type such as sieve trays, bubble cap trays and valve trays, or of packed column type packed with irregular packings such as pall rings or Raschig rings, or with regular packings such as sheet-like or gauze-like plates or composite plates consisting of a combination thereof.

The second gas introduced into the lower part of the absorption column 320 via the pipe 312 from the first reactor 310 countercurrently contacts the absorbing liquid for carbonate ester absorption (hereinafter simply referred to as the "absorbing liquid") introduced from the upper part of the absorption column 320. Thus, at least a part of the carbonate ester contained in the second gas is absorbed in the absorbing liquid by allowing the second gas and the absorbing liquid to gas-liquid contact. Accordingly, a condensate that absorbed the carbonate ester and the noncondensable gas containing nitric monoxide are obtained.

Examples of the absorbing liquid used in the absorption column 320 include alcohols corresponding to the alkyl group of the carbonate ester, carbonate esters and oxalate esters.

The amount of the absorbing liquid to be supplied to the absorption column 320 is, for example, 1 to 30% on a mass basis relative to the carbonate ester in the second gas. As the alcohol, the aliphatic alcohols having 1 to 3 carbon atoms such as methanol or ethanol are preferable. From the viewpoint of easy recovery, it is preferable that an alcohol have the same alkyl group with the alkyl nitrite introduced with the carbon monoxide to the first reactor 310.

The condensate containing the absorbing liquid and the carbonate ester obtained in the absorption column 320 is extracted from a pipe 314 connected to the bottom part of the absorption column 320. The condensate is introduced into the distillation column 360 through the pipe 314. In the distillation column 360, the condensate is separated into the solution containing the absorbing liquid and the first solution containing the carbonate ester based on the boiling point differences. When a low boiling point alcohol such as methanol or ethanol is used as the absorbing liquid, the alcohol is discharged from a pipe 362 connected to the column top part of the distillation column 360 and the first solution is discharged from a pipe 13 connected to the bottom part of the distillation column 360.

The first solution may be supplied to the treatment tank 10 in FIG. 1 or may be supplied to the first distillation column 20. The content of the alcohol in the first solution can be changed by adjusting the operation conditions of the distillation column 360. The content of the carbonate ester in the first solution is, for example, 98.0 to 99.998 mass %.

The noncondensable gas containing the carbon monoxide obtained in the absorption column 320 flows through a pipe 313 connected to the upper part of the absorption column 320. A pipe 322 for introducing the molecular oxygen is connected to the pipe 313. The molecular oxygen supplied from the pipe 322 is mixed with the noncondensable gas to be a mixed gas. The mixed gas flows through the pipe 313 and is introduced into the second reactor 330.

The mixed gas passed through the pipe 313 is introduced to the second reactor 330 from underneath and countercurrently contacts the alcohol (ROH) introduced from the pipe 316 connected to the above of the second reactor 330, whereby the reaction represented by the following reaction formula (I) proceeds. Due to this reaction, alkyl nitrite (RONO) is produced. In the formula (I), R represents an alkyl group. R is preferably an alkyl group having 1 to 3 carbon atoms. When the production apparatus 300 seen as the whole, the second reactor 330 functions to reproduce the alkyl nitrite.

In the second reactor 330, the side reaction represented by the reaction formula (II) may proceed. From the viewpoint of improving the efficiency of the entire facility, it is preferable to promote the reaction formula (I) than the reaction formula (II). The mixing ratio of the nitric monoxide and the molecular oxygen in the mixed gas may be 0.08 to 0.2 mol relative to per mol of the nitric monoxide contained in the mixed gas.

$$2NO+\tfrac{1}{2}O_2+2ROH \rightarrow 2RONO+H_2O \tag{I}$$

$$NO+\tfrac{3}{4}O_2+\tfrac{1}{2}H_2O \rightarrow HNO_3 \tag{II}$$

For the alcohol introduced from the pipe 316, an alcohol having the alkyl group of the carbonate ester produced in the production apparatus 300 is used. Examples of the alcohol include aliphatic alcohols having 1 to 3 carbon atoms such as methanol or ethanol. From the viewpoint of sufficiently proceeding the reaction of the reaction formula (I), the amount of the alcohol to be supplied to the second reactor 330 is, for example, 0.5 to 1.5 in a molar ratio relative to the supplied amount of the nitric monoxide contained in the mixed gas.

The reaction temperature at the second reactor 330 can be suitably determined in accordance with the kind of alcohol introduced from the pipe 316. For example, when methanol is used as the alcohol, the reaction temperature is, for example, 0 to 80° C. The reaction pressure is, for example, 0.1 to 1 MPa and the gas-liquid contact time is, for example, 0.5 to 30 seconds.

The third gas extracted from the upper part of the second reactor 330 contains, in addition to the alkyl nitrite produced by the reaction formula (I), nitric monoxide and trace components such as dinitrogen oxide and carbon dioxide. These trace components can be suitably discharged out of the system as an offgas from a pipe 317 branched from a pipe 311. The content of the nitric monoxide in the third gas is, for example, 5 to 50 vol % to the total of the nitric monoxide and the alkyl nitrite.

From a pipe 315 connected to the bottom part of the second reactor 330, water and the nitric acid produced by the reactions represented by the reaction formula (I) and the reaction formula (II) and the unreacted alcohol are discharged. These components may be processed to be reused as necessary by a recovery facility provided on the downstream side. Examples of the recovery facility include those wherein water, the nitric acid and the alcohol stored temporarily in a tank are introduced to a concentration column to separate the water and the alcohol from the nitric acid whereby nitric monoxide or carbon monoxide is reacted to the nitric acid and the alcohol to produce alkyl nitrite. The thus obtained alkyl nitrite may be introduced to the second reactor 330.

The third gas flows through the pipe 311 toward the first reactor 310. The pipe 311 has a merging part with a pipe 318 which supplies the carbon monoxide, and the third gas and the carbon monoxide are mixed in the merging part. Thus, the first gas is obtained. The first gas is supplied to the first reactor 310.

An embodiment of the present invention is described as above but the present invention is apparently not limited to the above embodiment. For example, it is not indispensable to carry out two distillation steps of the first distillation step and the second distillation step but one distillation step may be carried out.

EXAMPLE

Hereinafter, the present invention is further described in detail with reference to Examples and Comparative Examples, but is not limited to these Examples.

The analysis apparatus and analysis method in each Example to be described below are as follows.

Gas chromatograph GC-2014 (trade name), manufactured by Shimadzu Corporation, was used for the content analysis of organic compounds [dimethyl carbonate, methanol, dimethylene glycol dimethyl ether (MIME), methyl vinyl carbonate (MVC), methoxymethyl methyl carbonate (MMMC)]. HP-INNOWAX (trade name), manufactured by Agilent Technologies, was used as the capillary column.

Moisture meter model CA-05 (trade name), manufactured by Mitsubishi Chemical Corporation, was used for the analysis of the water content. For the analysis of the chlorine compound content, a sample was first pretreated using an oxy-hydrogen combustion type apparatus for analyzing the fixed quantity of sulfur/halogen, manufactured by TOKA SEIKI CO., LTD. Subsequently, using the pretreated sample, the $Cl^-$ content was measured using ion chromatograph measurement apparatus ICS-1600 (trade name), manufactured by Nippon Dionex K.K. Ion Pac AS12A (trade name), manufactured by Thermo Fisher Scientific Inc. was used as the separation column. The $Cl^-$ measurement limit (lower limit) in this analysis was 0.01 mass ppm.

The analysis of the nitric acid compound (including the nitrous acid compound) was carried out by extracting $NO_3^-$ and $NO_2^-$ from a sample using distilled water and subsequently using the ion chromatograph measurement apparatus used for the analysis of the Cr. The nitric acid compound (including the nitrous acid compound) measurement limit (lower limit) in this analysis was 0.01 mass ppm. In the analysis of the metal (Fe), a sample was first incinerated using a quartz dish and the incinerated product was dissolved in distilled water and high purity nitric acid (content: 69 to 70 mass %) to prepare a measurement sample. The obtained measurement sample was analyzed using an ICP-MS analyzer Agilent 7700 (trade name), manufactured by Agilent Technologies.

Example 1

<Alkali Treatment Step>

A stainless steel jacketed treatment tank (300 L) equipped with a thermometer and a stirrer was charged with 250 L of the dimethyl carbonate solution (the first solution) shown in Table 1. Warm water was allowed to pass through the jacket while stirring the dimethyl carbonate solution to adjust the solution temperature to be 40° C. A methanol solution with a sodium methylate content of 15 mass % (containing Na equimolar to Cl of 1.5 mass ppm in the first solution) was added to the dimethyl carbonate solution and continuously stirred for 1 hour. A part of the obtained treated solution was sampled and filtered, and the filtrate was analyzed. The composition of the filtrate was as shown in Table 1.

As shown in Table 1, it was verified that the addition of the alkali compound to the dimethyl carbonate solution can reduce the chlorine compound and the nitric acid compound. Additionally, it was verified that such an addition can reduce not only the chlorine compound and the nitric acid compound but also the methyl vinyl carbonate and the Fe component.

<First Distillation Step>

A glass distillation column (inner diameter: 25 mm, packing: Sulzer EX (registered trade name), number of theoretical plates: 16) equipped with a reflux pipe was prepared. A 300 ml-round bottom flask was attached to the bottom part of this distillation column. 200 ml of the filtrate of Table 1 was put in the round bottom flask.

The round bottom flask was immersed in an oil bath, which was heated and boiled for the total reflux. The total reflux was continuously carried out until the temperature of the entire distillation column reached substantially constant. When the temperature of the entire distillation column reached substantially constant, the temperature of the reflux liquid was 50 to 55° C. The filtrate shown in Table 1 was continuously supplied using a supply pipe connected to the middle of the distillation column in a flow rate of 150 ml/hour. At the same time of starting the supply, the liquid was continuously discharged from the round bottom flask in such a manner that the liquid surface in the round bottom flask was kept constant. A part of the reflux liquid was gradually discharged from the reflux pipe to obtain the distilled liquid while maintaining a reflux flow rate of 130 to 150 ml/hr and a column top temperature of the distillation column of 89° C. or more. The discharge volume of the distilled liquid from the column top was 2 to 3 ml/hr. Table 1 shows the analysis results of the distilled liquid discharged from the column top and the liquid discharged from the bottom.

<Second Distillation Step>

The discharged liquid from the bottom obtained in the first distillation step was supplied to a distillation column having 16 theoretical plates and provided with a regular packing, boiled under an ordinary pressure for the total reflux. Then, the distilled liquid was gradually discharged from the column top while maintaining a column top temperature of 90° C. or more. After discharged about 3 vol % of the supplied liquid volume from the column top, a reflux ratio was adjusted to be 1.5. Subsequently, the dimethyl carbonate solution was distilled off by a side cut arranged at a position ¼H lower from the column top (a height of ¾H from the column bottom) when the total height of the distillation column is defined as H. The composition of the dimethyl carbonate solution obtained by the side cut was as shown in Table 1.

TABLE 1

| Component | First solution | Filtrate | Distilled liquid from column top | Discharged liquid from bottom | Side cut |
|---|---|---|---|---|---|
| Dimethyl carbonate | 99.997% | 99.996% | 99.125% | 99.997% | 99.998% |
| Methanol | 4 ppm | 18 ppm | 198 ppm | 2 ppm | 2 ppm |
| Water | 21 ppm | 21 ppm | 17 ppm | 26 ppm | 10 ppm |
| Chlorine compound | 1.5 ppm | n.d. | n.d. | n.d. | n.d. |
| Nitric acid compound | 0.3 ppm | 0.2 ppm | 20 ppm | n.d. | n.d. |

TABLE 1-continued

| Component | First solution | Filtrate | Distilled liquid from column top | Discharged liquid from bottom | Side cut |
|---|---|---|---|---|---|
| DMME | 1 ppm | 1 ppm | 100 ppm | n.d. | n.d. |
| MVC | 1 ppm | n.d. | n.d. | n.d. | n.d. |
| MMMC | n.d. | n.d. | n.d. | n.d. | n.d. |
| Fe | 49 ppb | n.d. | n.d. | n.d. | n.d. |

Contents are mass base values. In the Table, "n.d." indicates below detectable limit.

As shown in Table 1, neither methoxymethyl methyl carbonate (MMMC) nor methyl vinyl carbonate (MVC) was detected in the filtrate, the distilled liquid from the column top, the discharged liquid from the bottom and the side cut. This finding verified that the dimethyl carbonate with sufficiently reduced impurities can be produced by the purification method of Example 1. The purity of the dimethyl carbonate in the discharged liquid from the bottom was 99.997 mass % and the purity of the dimethyl carbonate from the side cut was 99.998 mass %. This finding verified that the high purity dimethyl carbonate solution can be produced.

Example 2

The alkali treatment step, the first distillation step and the second distillation step were carried out in the same manner as in Example 1 except that a methanol solution in which a sodium methylate content was 5 mass % (containing Na equimolar to Cl of 1.5 mass ppm in the first solution) was used in place of the methanol solution in which a sodium methylate content was 15 mass %. The analysis results were as shown in Table 2.

TABLE 2

| Component | First solution | Filtrate | Distilled liquid from column top | Discharged liquid from bottom | Side cut |
|---|---|---|---|---|---|
| Dimethyl carbonate | 99.997% | 99.99% | 99.09% | 99.997% | 99.998% |
| Methanol | 4 ppm | 50 ppm | 550 ppm | 2 ppm | 2 ppm |
| Water | 21 ppm | 21 ppm | 17 ppm | 26 ppm | 10 ppm |
| Chlorine compound | 1.5 ppm | n.d. | n.d. | n.d. | n.d. |
| Nitric acid compound | 0.3 ppm | 0.2 ppm | 20 ppm | n.d. | n.d. |
| DMME | 1 ppm | n.d. | 100 ppm | n.d. | n.d. |
| MVC | 1 ppm | 1 ppm | n.d. | n.d. | n.d. |
| MMMC | n.d. | n.d. | n.d. | n.d. | n.d. |
| Fe | 49 ppb | n.d. | n.d. | n.d. | n.d. |

Contents are mass base values. In the Table, "n.d." indicates below detectable limit.

As shown in Table 2, neither methoxymethyl methyl carbonate (MMMC) nor methyl vinyl carbonate (MVC) was detected in the filtrate, the distilled liquid from the column top, the discharged liquid from the bottom and the side cut. This finding verified that the dimethyl carbonate with sufficiently reduced impurities can be produced by the purification method of Example 2. The purity of the dimethyl carbonate in the discharged liquid from the bottom was 99.997 mass % and the purity of the dimethyl carbonate from the side cut was 99.998 mass %. This finding verified that the high purity dimethyl carbonate solution can be produced.

Comparative Example 1

The alkali treatment step, the first distillation step and the second distillation step were carried out in the same manner as in Example 1 except that a methanol solution in which a sodium methylate content was 20 mass % (containing Na equimolar to Cl of 1.5 mass ppm in the first solution) was used in place of the methanol solution in which a sodium methylate content was 15 mass %. The analysis results were as shown in Table 3.

TABLE 3

| Component | First solution | Filtrate | Distilled liquid from column top | Discharged liquid from bottom | Side cut |
|---|---|---|---|---|---|
| Dimethyl carbonate | 99.997% | 99.995% | 99.287% | 99.995% | 99.998% |
| Methanol | 4 ppm | 18 ppm | 198 ppm | 2 ppm | 2 ppm |
| Water | 21 ppm | 21 ppm | 17 ppm | 26 ppm | 10 ppm |
| Chlorine compound | 1.5 ppm | n.d. | n.d. | n.d. | n.d. |
| Nitric acid compound | 0.3 ppm | 0.2 ppm | 20 ppm | n.d. | n.d. |
| DMME | 1 ppm | 1 ppm | 100 ppm | n.d. | n.d. |
| MVC | 1 ppm | n.d. | n.d. | n.d. | n.d. |
| MMMC | n.d. | 2 ppm | n.d. | 2 ppm | 2 ppm |
| Fe | 49 ppb | n.d. | n.d. | n.d. | n.d. |

Contents are mass base values. In the Table, "n.d." indicates below detectable limit.

As shown in Table 3, it was verified that the methoxymethyl methyl carbonate (MMMC) was produced in the alkali treatment step. The MMMC has been remained in the discharged liquid from the bottom obtained in the first distillation step and the side cut obtained in the second distillation step. Thus, the once produced MMMC could not be removed in the distillation steps.

INDUSTRIAL APPLICABILITY

According to the present disclosure, a carbonate ester purification method capable of reducing impurities and a carbonate ester purification apparatus can be provided. Further, a production method capable of producing a carbonate ester solution with reduced impurities can be provided.

REFERENCE SIGNS LIST

360 . . . Distillation column, 10 . . . Treatment tank, 13, 14, 15, 18, 21, 25, 26, 30, 36, 46, 49, 50, 60, 66 . . . Pipe, 12 . . . Jacket, 16 . . . Stirrer, 17 . . . Filtering device, 20 . . . First distillation column, 20A, 40A . . . Reflux part, 22, 42 . . . Condenser, 24, 44 . . . Tank, 19, 27, 34, 47, 64 . . . Pump, 32, 62 . . . Heat exchanger, 40 . . . Second distillation column, 48 . . . Heat exchanger, 100 . . . Treatment part, 101 . . . First distillation part, 102 . . . Second distillation part, 110 . . . Separation part, 200 . . . Purification apparatus, 300 . . . Production apparatus, 310 . . . First reactor, 320 . . . Absorption column, 330 . . . Second reactor.

The invention claimed is:

1. A carbonate ester solution production method comprising:
   an alkali treatment step of mixing a first solution containing a carbonate ester and an acidic substance with an alcohol solution of a metal alcoholate to obtain a mixed solution containing a reaction product of the acidic substance and the metal alcoholate;
   a removal step of removing a metal salt contained in the reaction product from the mixed solution using a filtering device provided with a filter to obtain a second solution containing the carbonate ester; and
   a distillation step of removing a component from the second solution, the component having a different boiling point from the carbonate ester to obtain a carbonate ester solution,
   wherein a content of the metal alcoholate in the alcohol solution is 5 to 18 mass %,
   and wherein the first solution is obtained by condensing a product obtained by gas phase reaction of carbon monoxide and nitrite in the presence of a platinum group metal solid catalyst.

2. The carbonate ester solution production method according to claim 1, wherein a content of a methoxymethyl methyl carbonate in the carbonate ester solution is less than 2 mass ppm.

3. The carbonate ester solution production method according to claim 1, wherein a purity of the carbonate ester in the carbonate ester solution is 99.99 mass % or more.

4. The carbonate ester solution production method according to claim 1, wherein the acidic substance contains at least one selected from the group consisting of nitric acid, a nitrous acid, a nitric acid compound and nitrous acid compound.

* * * * *